United States Patent [19]

Hüschelrath et al.

[11] Patent Number: 4,792,755

[45] Date of Patent: Dec. 20, 1988

[54] PROCESS AND APPARATUS FOR THE NON-DESTRUCTIVE EXAMINATION OF FERROMAGNETIC BODIES HAVING SECTIONS OF SURFACE ADJOINING EACH OTHER ALONG EDGES AND/OR AT CORNERS

[75] Inventors: Gerhard Hüschelrath, Laufach-Frohnhofen; Ekkehard Rehfus, Hürth, both of Fed. Rep. of Germany

[73] Assignee: Nukem GmbH, Hanau, Fed. Rep. of Germany

[21] Appl. No.: 884,364

[22] Filed: Jul. 11, 1986

[30] Foreign Application Priority Data

Jul. 16, 1985 [DE] Fed. Rep. of Germany ....... 3525376

[51] Int. Cl.$^4$ ..................... G01N 27/83; G01R 33/06
[52] U.S. Cl. ................................ 324/225; 324/235; 324/242; 324/262
[58] Field of Search ............... 324/220, 225, 227, 232, 324/233, 235, 242, 243, 262

[56] References Cited

U.S. PATENT DOCUMENTS

| | | | |
|---|---|---|---|
| 3,535,624 | 10/1970 | Wood | 324/220 X |
| 3,670,239 | 6/1972 | Shiraiwa et al. | 324/235 |
| 4,087,749 | 5/1978 | McCormack | 324/235 X |
| 4,258,319 | 3/1981 | Shimada et al. | 324/242 X |
| 4,288,747 | 9/1981 | Kawabata et al. | 324/243 X |
| 4,439,730 | 3/1984 | Kauffman | 324/232 |
| 4,460,869 | 7/1984 | Buser et al. | 324/227 X |
| 4,477,776 | 10/1984 | Spierer | 324/242 X |
| 4,485,344 | 11/1984 | de Sivry et al. | 324/262 X |
| 4,538,108 | 8/1985 | Huschelrath et al. | 324/235 X |
| 4,556,846 | 12/1985 | D'Hondt | 324/225 X |
| 4,564,809 | 1/1986 | Huschelrath et al. | 324/225 |
| 4,591,784 | 5/1986 | Kolitsch et al. | 324/227 X |
| 4,677,379 | 6/1987 | Arnaud et al. | 324/240 X |

FOREIGN PATENT DOCUMENTS

| | | |
|---|---|---|
| 3132808 | 1/1984 | Fed. Rep. of Germany. |
| 3416015 | 10/1985 | Fed. Rep. of Germany. |
| 3446867 | 7/1986 | Fed. Rep. of Germany. |

*Primary Examiner*—Gerard R. Strecker
*Attorney, Agent, or Firm*—Cushman, Darby & Cushman

[57] ABSTRACT

This invention relates to a process and an apparatus for the non-distructive examination of ferromagnetic bodies having sections of their surface adjoining along edges. The bodies or body parts are examined for structural faults or disturbances, including the regions along the edges and/or at the corners. A magnetic field is produced in the given body or body section. This field is stationary with respect to magnetic field sensors provided for measuring the stray fields on the surface. In a first measuring phase, measurements obtained for stray flux which are characteristic for the various positions of the magnetic field sensors along the surface of the body or body section are stored as reference values. In a second measuring phase, the reference values allocated to the various positions are subtracted from the stray flux values measured at these positions. The differences are then compared with predetermined threshold values.

11 Claims, 4 Drawing Sheets

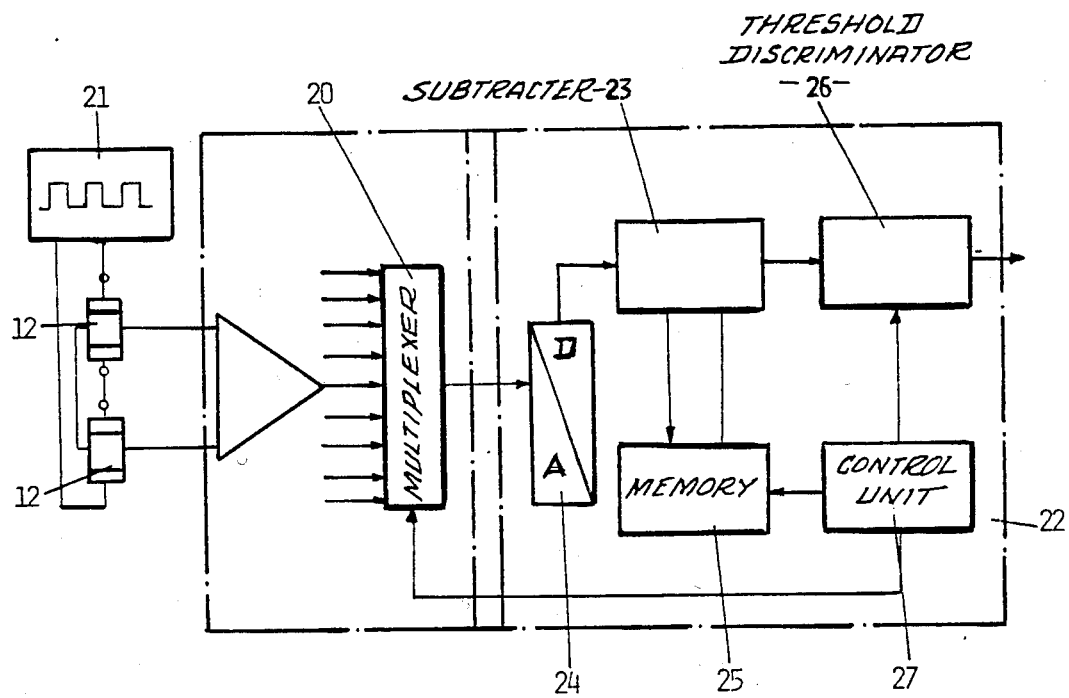
FIG.: 4
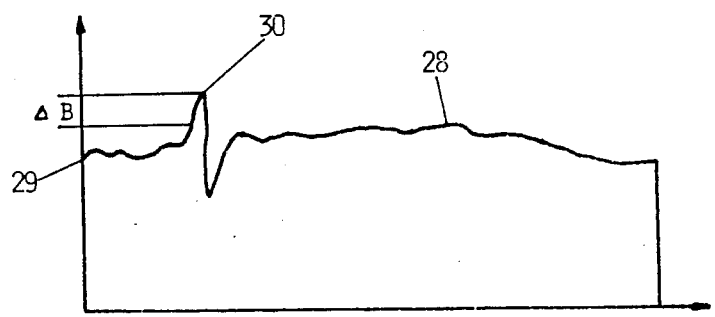
FIG.: 5

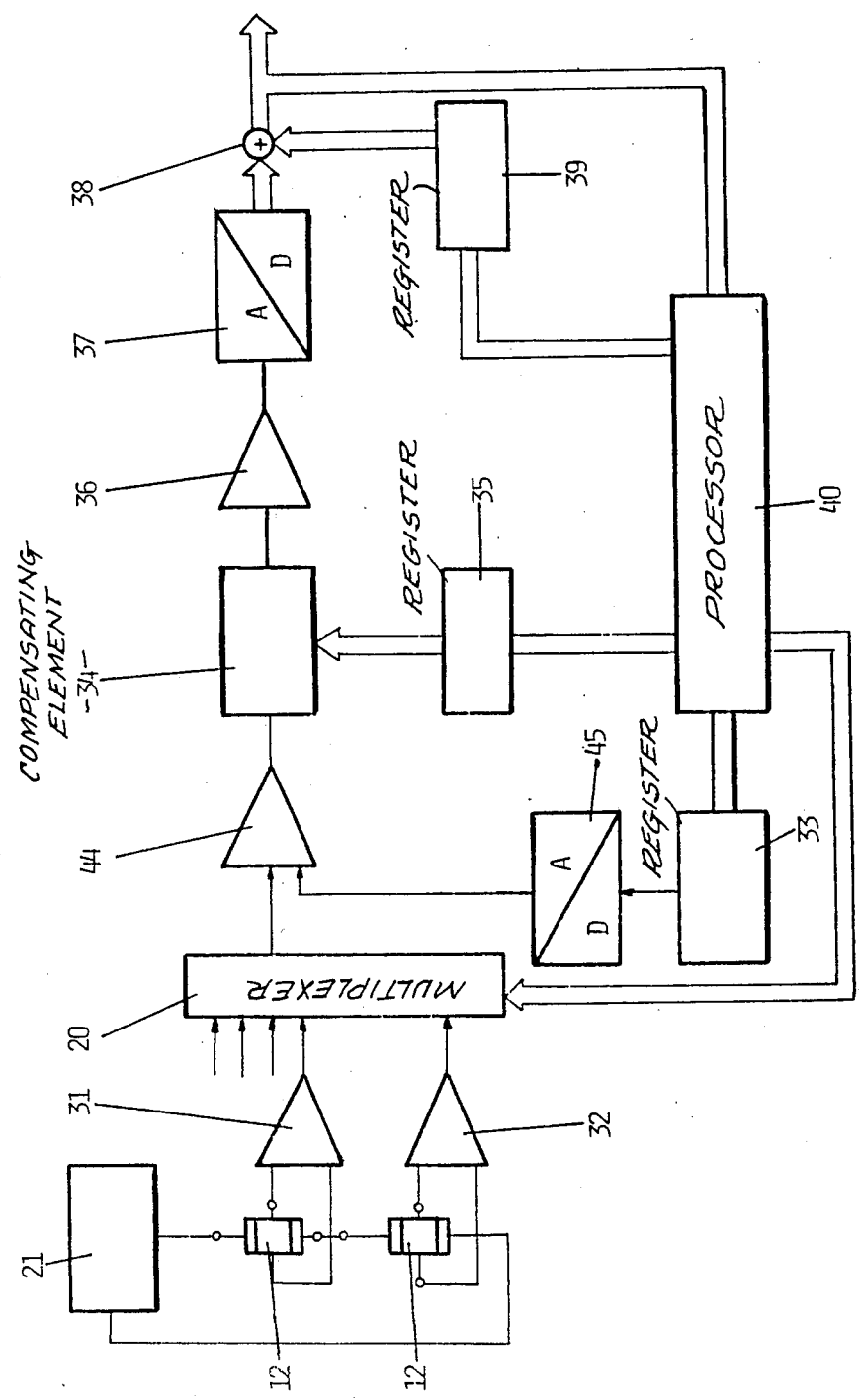

PROCESS AND APPARATUS FOR THE NON-DESTRUCTIVE EXAMINATION OF FERROMAGNETIC BODIES HAVING SECTIONS OF SURFACE ADJOINING EACH OTHER ALONG EDGES AND/OR AT CORNERS

BACKGROUND OF THE INVENTION

1. The Field of Art

This invention relates to a process for the non-destructive examination of ferromagnetic bodies or parts of bodies in which is produced a magnetic field whose stray fields extending outside the bodies or parts of bodies are measured by means of magnetic field sensors arranged on or above the surface.

2. Description of the Prior Art

Ferromagnetic bodies are measured non-destructively for structural faults by means of magnetic stray fluxes which, in the event of internal structural faults, occur outside the body surfaces due to stationary magnetic fields produced in the bodies. The stray fluxes are detected by magnetic field sensors arranged on or close to the body surfaces. An apparatus for non-destructive examination of ferromagnetic bodies has been described, for example, in DE-PS No. 3 132 808.

When the surface of bodies takes an irregular course, more powerful magnetic stray fields occur outside the body in the regions of these irregularities, e.g. at the edges and corners, and the magnitude of these fields frequently exceeds that of stray fields produced by structural faults in the interior of body sections which have a regular surface. Examination by means of magnetic stray fields has therefore hitherto been limited to bodies or body sections on which the surface takes a regular course and different methods of examining faults have been employed in the regions of edges, corners or ends of bodies. For example, these regions have been investigated for structural faults by means of magnetic powder testing or the color penetration test. Since these methods entail a visual control of the test sample, they are relatively time consuming and expensive.

It is an object of the present invention to develop a process for the non-destructive examination of ferromagnetic bodies having sections of surface adjoining along edges and/or at corners by which the detection of structural faults by means of the measurement of magnetic stray fields could also be carried out in the regions of the edges and/or corners.

SUMMARY OF THE INVENTION

The problem is solved according to the invention by the measurements described in claim 1. These measurements determine structural faults, i.e. faults in the material, by means of reference values. The examination is not based on absolute values but on relative values. The deviations of the measured values from a reference value are determined for each surface section under examination and compared with given threshold values.

If a body is symmetrical, reference values are preferably first measured (and stored) along a surface section. The surface section being measured is subsequently replaced by other surface sections by changing the position of the body or of the magnetic field sensors, and the magnetic stray fields of these other sections are then measured and compensated with the reference values. In the process described here, it is no longer necessary to obtain the reference values by means of a test sample which is free from structural faults. If no material faults exist under the surface section which is used for determining the reference values, then the values of stray flux measured when faults exits in the body lie above the reference values obtained in the corresponding position in the absence of faults. However, structural faults may be present in the part used for obtaining the reference values. These manifest themselves in correspondingly large reference values. When body sections free from faults are measured, their stray flux values will be smaller than the reference values. It will then be possible to localize the fault to the region from which the reference values were obtained.

An apparatus according to the invention for carrying out the process described in claims 1 and 2 has at least one magnetic field sensor placed at a small distance from the surface of the magnetizied body or body section to measure the course of the magnetized stray field on the surface thereof and an arrangement comprising a storage for reference values, a subtractor for the measured stray flux values and the reference values and a threshold value discriminator and connected in series with the magnetic field sensor. With this arrangement, the reference values of the stray field can be measured and fed into the storage in the first measuring phase. Compensation of the stray flux value with the reference values and can then be carried out in the second measuring phase, and any difference exceeding the threshold value indicates a fault.

For radially symmetric bodies or body sections it is advantageous to arrange magnetic field sensors at a small, constant distance apart in a row following the contours of the body or body section in a plane passing through the axis of symmetry of the body or body section and to mount the body or body section or the magnetic field sensors so as to be rotatable about the axis of symmetry. Such an arrangement may be used to carry out the first measuring phase on a stationary body. This first measuring phase supplies for each individual magnetic field sensor a reference value which is applicable to all surface locations which lie on a circular arc defined by the axis of rotation and the point to be measured and which are examined in the second measuring phase during rotation of the body.

Each row of magnetic field sensors advantageously is connected with a holder which is pivotally mounted and is displaceable into a testing position in which the magnetic field sensors are arranged at slight distances from the surface of the body to be tested.

The body to be tested is advantageously arranged to be fixed in its testing position in relation to the row or rows of magnetic field sensors by means of at least one abutment. The body may consist, for example, of an elongated, radially symmetrical section on which the surface takes a regular course, as for example, in the case of pipes which widen out at their ends to form sleeves. Examination of the middle section requires at least one longitudinal displacement of the pipes. The abutment terminates the longitudinal displacement and provides the precondition for rotation in the correct position in relation to the row of magnetic field sensors arranged on the holder.

In a preferred embodiment, at least two magnetic poles spaced apart are arranged close to the surface of the body or body section to be examined, and at least one magnetic field sensor is arranged between the two magnetic poles at equal distances from each pole close to the surface of the body or body section to be examined. The magnetic pole shoes produce a stationary (static) magnetic field which has its highest values for field intensity in the ferromagnetic body which is to be examined.

It is also advantageous to pass an electric current into the bodies to be examined in order to produce a magnetic field which gives rise to magnetic stray fields where structural faults occur. If the body to be examined is radially symmetrical, a current flowing in the axial direction is produced by suitably placed connections. It is then advantageous for the sake of obtaining a simple construction to provide the abutment in the form of an electrode.

If only one magnetic field sensor is used for the examination, this is advantageously fixed to the end of an arm of an electromechanical manipulating device which is programmed to move the end of the arm in the axial direction of a radially symmetrical body while the said body rotates.

BRIEF DESCRIPTION OF THE DRAWINGS

Further details, features and advantages of the invention will be apparent from the description given below with reference to an example of an embodiment illustrated in the drawings, in which FIG. 4 is a circuit diagram of an arrangement for processing the values of the magnetic fields measured by magnetic field sensors in the examination of the body shown in FIG. 1, FIG. 5 is a diagram representing the magnetic field strength on the surface of the body of FIG. 1 along a circular track which is concentric to the axis of symmetry and FIG. 6 is a circuit diagram of another arrangement for processing the magnetic field values measured by magnetic field sensors in the examination of the body of FIG. 1.

DETAILED DESCRIPTION OF THE PREFERRED EMBODIMENT

Figure 1:
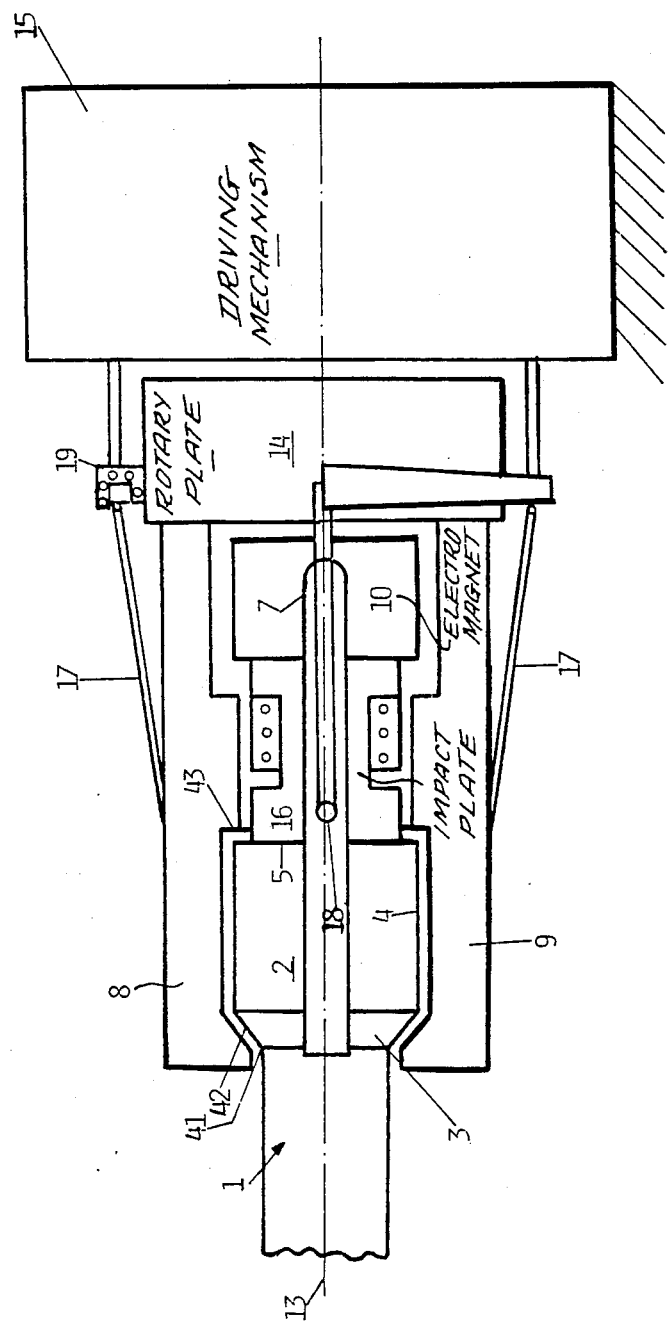
FIG. 1 represents a side view of an apparatus for the non-destructive examination of a radially symmetrical ferromagnetic body in the form of a pipe which widens out of the end in the form of a sleeve.

Referring to FIG. 1, a body 1 to be examined in the form of a tube having an end 2 in the form of a sleeve, also referred to as body section 2, which has a section 3 in the form of a truncated cone extending from the tube, a cylindrical section 4 and an annular end face 5.

Two magnetic pole shoes 6,7 are strayed at diametrically opposite sides of the end 2. The surfaces of the pole shoes 6,7 facing the end 2 are adapted to the contour of that part of the surface of the end 2 which they face. The pole shoes 6,7 therefore embrace the end 2 at the end face 5 and the section 3.

The pole shoes 6,7 produce a magnetic field in the end 2. If the material is free from faults, this magnetic field lies substantially inside the ferromagnetic body 1 or the end 2. If structural faults are present in the body 1 or end 2, stray fluxes extending to the outside of the body 1 or end 2 are formed and these fluxes are measured by magnetic field sensors.

Figure 3:
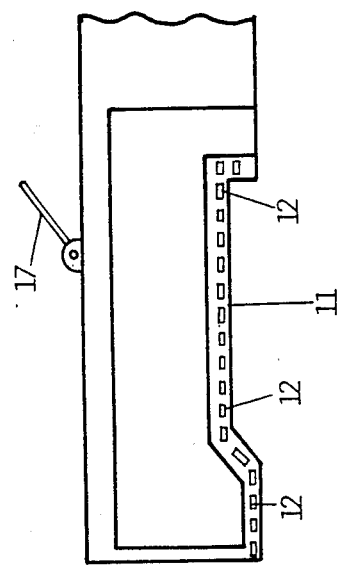
FIG. 3 represents a side view of a holder for magnetic field sensors.
Figure 2:
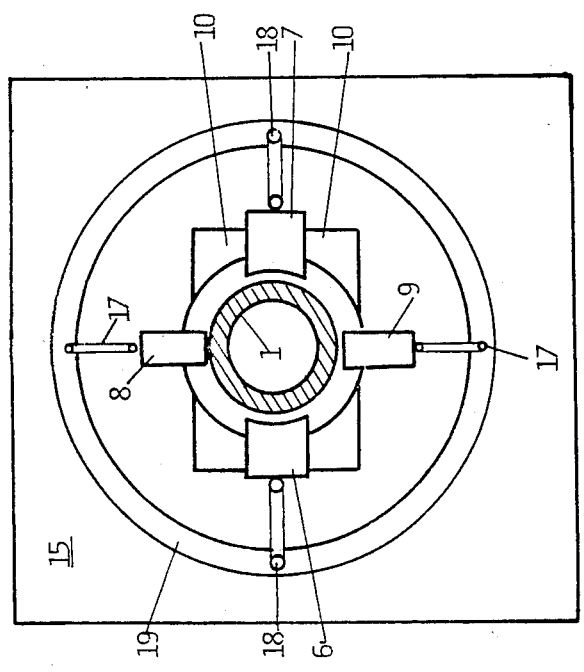
FIG. 2 represents a front view of the apparatus illustrated in FIG. 1.

The magnetic field sensors are attached to two holders 8,9 which are situated at two diametrically opposite locations at a slight distance from the surface of the end 2. The holders 8,9 with magnetic field sensors are situated halfway between the pole shoes 6,7. The two pole shoes 6,7 are mounted on a yoke which consists of an electromagnetic 10. The contour 11 of the holders 8,9 on the sides facing the end 2 follows the contour of the section 3, the section 4 and the end face 5, as indicated in FIG. 3. The holders 8,9 carry magnetic field sensors 12 in the surface facing the end 2, for example in grooves (not shown). These sensors are arranged in a row in the longitudinal direction of the body 1 or the end 2. They follow the course of the end 2 at a short distance from the surface of this part (i.e. they follow a contour obtained from the lines of intersection of a plane passing through the axis of symmetry 13 of the body 1) with the external surfaces of the body 1. The magnetic field sensors 12 are preferably Hall generators. Two layers of Hall generators, for example, may be arranged one above the other with any two Hall generators lying one above the other in the same position being electrically connected together by a differential connection. The Hall generators may be placed either with their broad sides or their narrow sides above one another. The axis of symmetry 13 of the body 1 with end 2 is also the longitudinal axis of this structure.

Each holder 8,9 is pivoted at one end to a rotary plate 14 to serve as abutment for the end face 5 of the plate 14 to which the electromagnet 10 is also attached. A driving mechanism 15 mounted in a fixed position sets into rotation the rotary plate 14 together with the parts 6,7,8,9 and 10 attached thereto while the tube 1 remains stationary. An impact plate 16 is attached to the rotary end 2. The impact plate 16 stops the longitudinal displacement of the tube 1 and centres the tube with respect to the magnetic pole shoes 6,7 and the holders 8,9. The holders 8,9 and magnetic pole shoes 6,7 are connected by links 17,18 to a ring 19 which is mounted to be displaceable in the axial direction of the rotary plate 14. The holders 8,9 and pole shoes 6,7 which are pivotally attached to the rotary plate 14 can be deflected about their pivot pins by longitudinal displacment of the links 17,18.

The body 1 is examined for structural faults, for example by means of an apparatus described in DE-PS No. 3 132 808. This examination covers only the cylindrical part in the middle of the tube while the end 2 of the body is examined by means of the apparatus illustrated in FIGS. 1 to 4. Examination of the kind described in DE-PS No. 3 132 808 is completed when the end face 5 of the body 1 abuts against the impact plate 16 which terminates the longitudinal displacement of the body 1. At this stage, the ring 19 has been displaced in relation to the driving mechanism 15 so that the holders 8,9 and magnetic pole shoes 6,7 are spread apart in the manner of shears. When the end 2 is in its end position determined by the impact plate 16, the holders 8,9 and the magnetic pole shoes 6,7 are swung over the end 2.

The magnetic field sensors 12 are connected e.g. pairwise as gradient probes to inputs of a multiplexer 20 by way of differential amplifiers. FIG. 4 shows only two magnetic field probes 12 which are subjected to control pulses from a timing pulse generator 21. The multiplexer 20 has numerous other inputs connected to gradient probes, as indicated by arrows in FIG. 4.

An evaluating circuit 22 containing an analog-digital converter 24 and a substracter 23 fed by the analog—digital converter 24 is connected to the multiplexer 20. An analog subtracter could be used, in which case the analog—digital converter 24 may be omitted. A memory 25 into which data may be read from the subtracter 23 and which delivers substrahends to the subtracter 23 is connected to an input of the subtracter 23. Connected in series with the subtracter 23 is a threshold value discriminator 26 which may be selectively supplied with adjustable threshold values by way of a control unit 27 which also controls the input and output of data with the memory 25 and the adjustment of the multiplexer 20.

When the magnetic pole shoes 6,7 and the holders 8,9 are situated in their position for examination opposite the end 2, the electromagnet 10 is switched on to produce a magnetic field in the end 2. This field is stationary (static) in relation to the magnetic field sensors and high field strengths are substantially confined to the ferromagnetic end 2 if no structural faults are present. The edges 41,42,43 of the end 2, however, give rise to stray fluxes which may reach values equal to those due to structural faults. The course of the magnetic stray field is measured by the magnetic field sensors 12. Each magnetic field sensor is associated with a specific position on the surface of the body 1 or end 2. The value of stray flux measured in this position is stored in the memory 25 under an address allocated to this position. The stray flux may, for example, take the course indicated by 28 in FIG. 5 along a circular track on the surface of the end concentric to the longitudinal axis 13. There is preferably no relative displacement between the body 1 and the holders 8,9 and magnetic pole shoes 6,7 during the first measurement of the stray field. A stray flux of amplitude 29, for example, is then measured in this position by one of the magnetic field sensors 12 and stored in memory. This value of stray flux is used as reference value. Stray flux values are measured similarly by other magnetic flux sensors 12 and stored as reference values. Determination and storage of the reference values takes place during a first measuring phase. The reference values may be obtained from a test sample which is free from structural faults.

It is, however, immaterial whether or not a structural fault exists at the particular place where a reference value is determined. Evaluation of the measured values of stray flux are merely related to the reference values. The presence or absence of a structural fault in the location of the body or part where a reference value is obtained therefore only affects the sign of the value of stray flux measured.

In a second measuring phase, the holders 8,9 and magnetic pole shoes 6,7 are set into rotation. The stray fields are measured during this rotation and subtracted from the stored reference values in the subtracter 23. The test apparatus may, for example, execute one rotation. The values of stray field measured are thus compensated with the reference values. Only the stray flux values measured in a given magnetic field sensor are subtracted from a reference values measured with the same magnetic field sensor. The results of the subtraction are examined in the threshold value discriminator to ascertain whether a preset threshold value which is a measure for the existence of a structural fault has been exceeded.

FIG. 5 illustrates by way of example the amplitude 30 of a stray flux value caused by a structural fault. The difference between the amplitude 30 and the reference value 29 exceeds the adjusted threshold value $\Delta B$, with the result that the threshold value discriminator 26 signals a fault.

During one complete revolution of the body under examination, the two diametrically opposite rows of magnetic field sensors 12 are supplied with simultaneously measured reference values. The measurement over an angle of rotation of 360° produces more than one value of stray flux per measuring point on the body. The two values of stray flux obtained for each point measured are compared. This device has the advantage that interfering pulses can be detected and shut out.

If the differences between the stray fields existing with and without structural faults on the various locations of the body under examination are very large, magnetic field probes having a wide range of magnetic fields with a linear characteristic should be used.

The method of measurement described above is based on the principle of comparing stray flux values at different locations associated with the positions of the magnetic field sensors on the sample under investigation. The results to be evaluated are then not absolute values but relative values. This method of examination is possible because each magnetic field sensor may have its own reference value for compensating the measured values.

The measurement may also be carried out without the use of a fault-free test sample to provide reference values. In that case, the body 1 to be examined is itself used as provider of the reference values. A stuctural fault is generally not found during the first measuring phase but if such a fault does happen to be found then the amplitude 30, for example, is stored as reference value even though this is a value corresponding to a fault in the material. When this reference value is compared with the majority of stray flux values obtained along the same path of the end 2 on locations free from faults, the threshold value discriminator 26 responds when the absolute values of the differences are fed into it. It is then immediately obvious that the location at which the referece value was measured must contain a fault in the material, and correction for the reference value can then carried out.

The magnetic field required for examining by the stray flux method may also be produced by means of a current flowing over the body 1 in its axial direction. The impact plate 16 is then in the form of a contact electode while the other electrode may be, for example, a sliding contact. This arrangement dispenses with the magnetic pole shoes 6,7 and the electromagnet 10. The measurement is otherwise carried out in the same manner as described above.

If magnetization is carried out by means of a current, the whole sample under investigation or the whole region to be investigated may be covered by magnetic field sensors. No relative displacement between the sample and the magnetic field sensors is then necessary. The examination may be carried out very rapidly. The reference values are preferably obtained by means of a fault-free sample.

Bodies 1 to be examined may also be scanned with a single magnetic field sensor moved in various directions while the body 1 or end 2 remains in the same position during the examination. If the body is radially symmetrical, for example, it may be rotated during the examination while the magnetic field sensor is displaced in axial and/or radial directions of the body by means of an electromechanical operating device which is programmed to a particular part extending at a short distance from the contour of the body under examination.

The examination may also be carried out on sheets and their marginal zones, using the same magnetic field sensors and the same arrangement for evaulating the results, the mechanical arrangement of the magnetic field sensors being adjusted to the structural form of the bodies under examination.

The threshold values may be given in the form of signal deviations and their frequency portions.

The arrangement in FIG. 6 is shown with two magnetic field sensors 12 and their connecting electrodes. The nature of the circuit connections of all other magnetic field sensors 12 forming pairs is similar to that of the two magnetic field sensors shown in FIG. 6.

The supply electrodes for the control current for the magnetic field sensors 12 are connected in series. The pulse timing generator 21 feeds the supply electrodes for the control current. In the magnetic field sensors 12, the electrodes for tapping the Hall voltage are connected to an input of an amplifier 31, 32.

The timing pulse generator 21 produces a pulse sequence with a pulse interval to duration ratio of 1:10.

The outputs of the amplifiers 31,32 are connected to the inputs of the multiplexer 20 to which are also connected the amplifiers (not shown) which are supplied from the other magnetic field sensors 12. The multiplexer 20 is connected to an input of a compensation amplifer 44 by its output to which are transmitted the analog signals delivered by the amplifiers 31,32 or other amplifiers (not shown).

The compensation amplifier 44 is a differential amplifier. The second input of this differential amplifier receives its supply from a digital-analog converter 45 which has its digital inputs connected to a first register 33. The output of the compensation amplifier 44 is connected to a multiplying compensating element 34 which is supplied with the multiplication coefficient by way of another register 35. An amplifier 36 conected to the output of the compensating element 34 is connected in series with an analog-digital converter 37. The output of the analog-digital converter 37 is connected to the first inputs of an adder 38 which has its second inputs connected to an additional register 39. The outputs of the adder 38 are connected to inputs of a processor 40 which has outputs connected to the inputs of the registers 33,35 and 39. The processor 40 is also connected to the control inputs of the multiplexer 20.

The position of each of the magnetic field sensors 12 with regard to body 1 influences the Hall voltages $U_H$ of the magnetic field sensors 12 connected in series. This influence must be eliminated if high accuracy of measurement is to be achieved. The processor 40 contains a memory (not shown) which stores the reference values for the various positions of the magnetic field sensors 12. The reference values relate both to the central arrangement of the body 1 and to eccentric positions. The Hall voltages transmitted to the compensation amplifier 44 are then corrected by means of the compensation values from the register 33.

When the output of the multiplexer 20 is switched over to another input, that reference value which is allocated to the magnetic field sensor connected to this input is fed into the register 33.

Since the multiplexer 20 already has a certain amplification, e.g. in the region of 100 to 1000, the various Hall generators give rise to considerable differences in level at the output of the multiplexer 20, and these differences must be reduced to reduce the errors in measurement. The reference values which are dependent upon the position of the magnetic field probes are supplied to the compensation amplifier 44 by way of the digital analog converter 45. All large errors of indication and residual levels from the magnetic field distribution can thus be eliminated.

However, not only purely additive but also multiplicative values accumulate over the cross-sections of the Hall generators. These are due to the fact that the sensitivity characteristic curves of the Hall generators scatter and that the differences in field strength distribution give rise to fault indications differing in magnitude. These faults can be compensated for by the multiplying compensating element 34. The multiplication coefficient stands in readiness in the register 35 in dependence upon the probe. It is only after this compensation that the signals are amplified to the final level by the amplifier 36 before they are digitalized by the A/D converter 37. Since further tolerances are produced by the various stages of processing and the residual tolerances are further amplified, the final compensation takes place in the adder 38. The compensation values are deposited in the register 39 in dependence upon the probes.

This compensation in three stages is carried out for dynamic reasons. Since A/D conversion does not produce the necessary high resolution within the required time, interference levels should be suppressed before the amplification proper.

The multiplying compensating element 34 may be an analog multiplier. In that case, a digital-analog converter should be connected in series with the register 35. Since such analog multipliers also exert an amplifying function, the amplifier 36 may in many cases be omitted. Alternatively, a multiplying digital analogue converter having its digital inputs connected to the register 35 may be used as compensating member 34.

The arrangement shown in FIG. 6 resembles the arrangement of FIG. 4 in having a threshold value discriminator which is realised by the processor 40. The compensation amplifier 44 corresponds to the subtracter 23 of FIG. 4.

The method described above be used for detecting structural faults in the ends of tubes without the use of magnetic powder instruments. Another special advantage of this method is that faulty indications such as may occur in magnetic powder testing can be avoided by making a comparison of patterns by means of finned tubes.

It is advantageous to use two Hall generators for measuring the gradients of magnetic stray fields. The two Hall generators are preferably arranged with their broad sides on a flat supporting substrate at some distance apart along a common line with identical orientation with respect to the line and close to the edges of two opposite sides of the supporting substrate which are free from connections. Since the Hall generators are then no longer arranged with their broad sides one above the other but side by side, numerous such units may - be arranged side by side since they are effectively comparatively thin. The units in this arrangement face each other along their broad sides. This enables the surface of the body 1 under examination to be more accurately allocated to the different Hall generators. Structural faults or the like can therefore be more accurately localized and even relatively small faults in the body under examination can be detected.

One such arrangement is described in German Patent Application P No. 34 35 455.7. An apparatus capable of providing measurements of stray fluxes which are to a large extent independent of the position of the given magnetic field detector and the scattering of the parameters of the magnetic field detectors even when the magnetic field detectors produce powerful output signals may be arranged in front of the analogue-digital converter 24. Such an apparatus contains a compensation amplifier arranged in series with the multiplexer 20 and connected to an input of a multiplying compensating element. The other inputs of this compensating element may be subjected to the action of multiplication coefficients which compensate for the influences on the signals due to scattering of the sensitivity characteristic curves of the magnetic field detectors and the differing intensities of the magnetic field. The product produced by the compensating element is transmitted to the analog-digital converter 24 after amplification. The analog-digital converter 24 is advantageously connected in series with an adder into which compensation values allocated to the individual magnetic field detectors may be supplied through its second inputs to compenate for the influences due to tolerances in the circuit elements before the adder. Such an arrangement is described in detail in German Patent Application P No. 34 46 867.

The arrangements described in German Patent Applications Nos. 34 16 015 and No. 34 46 615 may also be used in conjunction with the arrangement described above.

The comparison of patterns mentioned above in the testing of tubes with fins is described in detail in German Patent Application No. 34 35 442.5. In this process, compensation values are allocated to given positions of the magnetic field detectors in relation to the welding seam. These compensation values are subtracted with the appropriate sign from the values of stray flux measured by the magnetic field detectors. The corrected values are checked for the presence of structural faults by comparing them with previously determined threshold values. Fresh compensation values are allocated for lateral changes in the positions of the magnetic field detectors relative to the welding seam according to the actual position of the magnetic field detector in relation to the welding seam before the correction with the measured values is carried out.

We claim:

1. A method for non-destructively examining at least corners or edges or radially symmetric ferromagnetic bodies rotatable about an axis of symmetry thereof, said corners or edges contoured along the axial direction of said body, comprising the steps of:
   producing a static magnetic field in said body;
   measuring in a first measuring phase, to obtain first measured stray flux values, magnetic stray fields extending outside said body along the axial direction of said body on or over at least a section of a contoured edge or corner surface of said body and also situated at a location so that other sections of said edge or corner surface of said body can be measured as a result of changes in relative position between said body and said location;
   storing first measured values of said stray flux measurements as compensation values with reference to said location at which said measurements arise along said section of said surface;
   rotating said body so that said other sections of said contoured edge or corner surface are successively positioned at said location;
   measuring in a second measuring phase a plurality of stray fluxes of said other sections of said edge or corner surface of said body to obtain second measured stray flux values;
   subtracting said second measured stray flux values measured at said other sections of said edge or corner surface from said compensation value allocated to said location to obtain difference values;
   comparing said difference values with predetermined threshold values; and
   indicating a structural fault exists when said difference values are of greater magnitude than said predetermined threshold values, wherein stray fields due to edge or corner contours are compensated.

2. The method according to claim 1 wherein:
   said step of measuring in a first measuring phase uses two sets of magnetic field sensors, each set of magnetic field sensors being placed along one of two diametrically opposite sections of said body to measure said stray magnetic fields at locations of said both sets of magnetic field sensors;
   said moving step rotates said body through 360°;
   said second measuring phase measures said other body sections during each half rotation on the basis of their correct location with respect to said body to obtain two stray flux values for each body surface measured, said second measuring step also including a comparing means which compares said two stray values to detect and short out interfering phases to obtain said second measured stray flux values.

3. An apparatus for non-destructively examining at least corners or edges of radially symmetric ferromagnetic bodies rotatable about an axis of symmetry thereof, said corners or edges being contoured along the axial direction of said body, comprising:
   means for generating a static magnetic field so that stray fields of said static magnetic field extend outside said body;
   magnetic field sensing means for measuring stray flux values of said stray fields positioned at a location to follow contours of a first section of the surface of said body along the axial direction thereof at least along edges or corners at a slight and constant distance therefrom in a plane passing through an axis of symmetry of said body;
   means for rotating said body about said axis of symmetry so that other sections of said edge or corner surface of said body are succesively positioned at said location;
   memory means for storing compensation values obtained by and associated with said magnetic field sensing means with respect to said first section;
   means for subtracting stray flux values measured at each successive section of said body surface by said magnetic field sensing means from said compensation values associated with said magnetic field sensing means to obtain a difference signal for each section of body surface measured; and
   means for threshold discrimination of said difference signals of a magnitude greater than a predetermined threshold to determine if a structural fault exists, wherein stray fields due to edge or corner contours are compensated.

4. An apparatus according to claim 3 further including:
- a multiplying equalizer which has inputs consisting of said difference and also predetermined multiplication coefficients which compensate for detected changes which are of a disproportionate size to actual values of the structural faults detected, said multiplying equalizer outputting a compensated difference; and
- an adder which adds said compensated difference to a predetermined fault compensation value, said adder outputting a result of this addition to said threshold discrimination means.

5. Apparatus according to claim 3 wherein said magnetic field sensing means includes a plurality of magnetic field sensors arranged along said section of said contoured edge or corner surface and further including a holder to which said magnetic field sensors are connected and which is pivotally mounted and to be moveable into a position for examination in which said magnetic field sensors are arranged at slight separation distances from said body under examination.

6. Apparatus according to claim 5, including a stop which fixes a longitudinal position of said body under examination for examination in relation to said row of magnetic field sensors.

7. Apparatus according to claim 3, wherein said means for generating a static magnetic field includes at least two magnetic pole shoes arranged at some distance apart and close to said surface of said body under examination, and wherein said magnetic field sensing means includes at least one magnetic field sensor arranged between said two magnetic poles, equidistant from said two magnetic poles arranged at a slight separation distance from said surface of said body under examination.

8. Apparatus according to claim 3 wherein said means for generating a static magnetic field includes means for passing an electric current into said body under examination for producing said static magnetic field and causing magnetic stray fields in the event of structural faults.

9. Apparatus according to claim 6, wherein said means for generating a static magnetic field includes means for passing an electric current into said body under examination for producing said static magnetic field and causing magnetic stray fields in the event of structural faults and wherein said stop includes a contact electrode for conducting said electric current to said body.

10. Apparatus according to claim 3, wherein said magnetic field sensing means includes a single magnetic field sensor and further includes an electromechanical manipulating device with an arm, said single magnetic field sensor being fixed to said arm.

11. Apparatus according to claim 7, further including means for pivotably mounting said magnetic pole shoes.

* * * * *